United States Patent [19]

Ruoslahti et al.

[11] Patent Number: 5,453,489
[45] Date of Patent: Sep. 26, 1995

[54] POLYPEPTIDE FRAGMENTS OF FIBRONECTIN WHICH CAN MODULATE EXTRACELLULAR MATRIX ASSEMBLY

[75] Inventors: Erkki I. Ruoslahti, Rancho Santa Fe; Alex Morla, San Diego, both of Calif.

[73] Assignee: La Jolla Cancer Research Foundation, La Jolla, Calif.

[21] Appl. No.: 829,462

[22] Filed: Jan. 31, 1992

[51] Int. Cl.[6] .............................. C07K 13/00; C07K 7/10; A61K 37/02
[52] U.S. Cl. .......................... 530/350; 530/324; 530/395
[58] Field of Search .................................. 530/324, 350, 530/381, 395; 514/12; 424/85.8; 435/69.1

[56] References Cited

U.S. PATENT DOCUMENTS

| | | | |
|---|---|---|---|
| 4,578,079 | 3/1986 | Ruoslahti et al. | 623/11 |
| 4,589,881 | 5/1986 | Pierschbacher et al. | 623/11 |

OTHER PUBLICATIONS

Hayashi, M., et al. (1981) J. Biol. Chem. 256: 11292–11300.
Calaycay, J., et al. (1985) J. Biol. Chem. 260: 12136–12141.
Akiyama et.al., Analysis of Fibronectin Receptor Function with Monoclonal Antibodies: Roles in Cell Adhesion, Migration, Matrix Assembly, and Cytoskeletal Organization. J.Cell Biol., 109: 863–875 (1991).
Ali and Hynes, Role of Disulfide Bonds in the Attachment and Function of Large, External, Transformation–Sensitive Glycoprotein at the Cell Surface. Biochim. Biophys. Acta. 510:140–150 (1978).
Chernousov et.al., Role of the I–9 and III–1 Modules of Fibronectin in Formation of an Extracellular Fibronectin Matrix. J. Biol. Chem. 266: 10851–10858 (1991).
Ehrismann et.al., Mode of Action of Fibronectin in Promoting Chicken Myoblast Attachment, Mr=60,000 gelatin-binding fragment binds native fibronectin. J. Biol. Chem. 256:4056–4062 (1981).
Ehrismann et.al., Arrangement of Attachment–Promoting, Self–Association, and Heparin–Binding Sites in Horse Serum Fibronectin. J. Biol. Chem. 257: 7381–7387 (1982).
Fogerty et.al., Inhibition of Binding of Fibronectin to Matrix Assembly Sites by Anti–integrin (alpha 5 beta 1) Antibodies. J. Cell Biol. 111: 699–708 (1990).
Giancotti and Ruoslahti, Elevated Levels of the Alpha 5 Beta 1 Fibronectin Receptor Suppress the Transformed Phenotype of Chinese Hamster Ovary Cells. Cell 60: 849–859 (1990).
Hynes and Destree, Extensive Disulfide Bonding at the Mammalian Cell Surface. Proc. Natl. Acad. Sci. U.S.A. 74:2855–2859 (1977).
Keski–Oja et.al., Dimeric Character of Fibronectin, a Major Cell Surface–Associated Glycoprotein. Biochem. Biophys. Res. Commun. 74: 699–706 (1977).
McDonald, J. A., Extracellular Matrix Assembly. Annu. Rev. Cell Biol. 4: 183–207 (1988).
McDonald et.al., Fibronectin Cell–Adhesive Domain and an Amino–Terminal Matrix Assembly Domain Participate in it Assembly into Fibroblast Pericellular Matrix. J. Biol. Chem. 262: 2957–2967 (1987).
McKeown–Longo et.al., Interaction of the 70,000–mol–wt Amino–terminal Fragment of Fibronectin with the Matrix–assembly Receptor of Fibroblasts. J. Cell Biol. 100: 364–374 (1985).

(List continued on next page.)

*Primary Examiner*—Garnette D. Draper
*Assistant Examiner*—David L. Fitzgerald
*Attorney, Agent, or Firm*—Campbell and Flores

[57] ABSTRACT

In accordance with the present invention, there is provided a novel synthetic polypeptide derived from the first type III repeat of fibronectin. The synthetic polypeptide of the invention encompasses a fibronectin-fibronectin binding site, and is capable of inhibiting fibronectin matrix assembly. In contrast to previously identified fibronectin fragments that block fibronectin matrix assembly by blocking an initial event in matrix assembly (i.e., fibronectin binding to cells), the invention polypeptide appears to inhibit an intermediate step in matrix assembly, i.e., fibronectin self-association prior to the disulfide cross-linking that stabilizes the fibronectin matrix.

6 Claims, 11 Drawing Sheets

OTHER PUBLICATIONS

Mosher et.al., Assembly of Fibronectin into Extracellular Matrix. Ann. N.Y. Acad. Sci. 614: 167–180 (1991).

Nagai et.al., Monoclonal Antibody Characterization of Two Distant Sites Required for Function of the Central Cell–Binding Domain of Fibronectin in Cell Adhesion, Cell Migration, and Matrix Assembly. J. Cell Biol. 114: 1295–1305 (1991).

Oh et.al., Deposition of Plasma Fibronectin in Tissues. Prod. Natl. Acad. Sci. U.S.A. 78: 3218–3221 (1981).

Peters and Mosher, Localization of Cell Surface Sites Involved in Fibronectin Fibrillogenesis. J. Cell Biol. 104: 121–130 (1987).

Peters et.al., Co–assembly of Palsma and Cellular Fibronectins into Fibrils in Human Fibroblast Cultures. J. Cell Biol. 111: 249–256 (1990).

Pierschbacher et.al., Cell Attachment Activity of Fibronectin can be Duplicated by Small Synthetic Fragments of the Molecule. Nature 309: 30–33 (1984).

Pierschbacher et.al., Synthetic Peptide with Cell Attachment Activity of Fibronectin. Proc. Natl. Acad. Sci. U.S.A. 80: 1224–1227 (1983).

Pierschbacher et.al., Variants of the Cell Recognition Site of Fibronectin That Retain Attachment–promoting Activity. Proc. Natl. Acad. Sci. U.S.A. 81: 5985–5988 (1984).

Pytela et.al., Identification and Isolation of a 140 kd Cell Surface Glycoprotein with Properties Expected of a Fibronectin Receptor. Cell 40: 191–198 (1985).

Quade and McDonald, Fibronectin's Amino–terminal Matrix Assembly Site is Located Within the 29–kDa Amino–terminal Domain Containing Five Type I Repeats. J. Biol. Chem. 263: 19602–19609 (1988).

Ruoslahti, E., Fibronectin and its Receptors. Annu. Rev. Biochem. 57: 375–413 (1988).

Ruoslahti, E., Integrins. J. Clin. Invest. 87:1–5 (1991).

Schwarzbauer, J. E., Identification of the Fibronectin Sequence Required for Assembly of a Fibrillar Matrix. J. Cell Biol. 113: 1463–1473 (1991).

Schwarzbauer, et.al., Efficient and Stable Expression of Recombinant Fibronectin Polypeptides. Proc. Natl. Acad. Sci. U.S.A. 84: 754–758 (1987).

Woods et.al., Fibronectin Fibril Formation Involves Cell Interactions With Tow Fibronectin Domains. Exp. Cell Res. 177: 272–283 (1988).

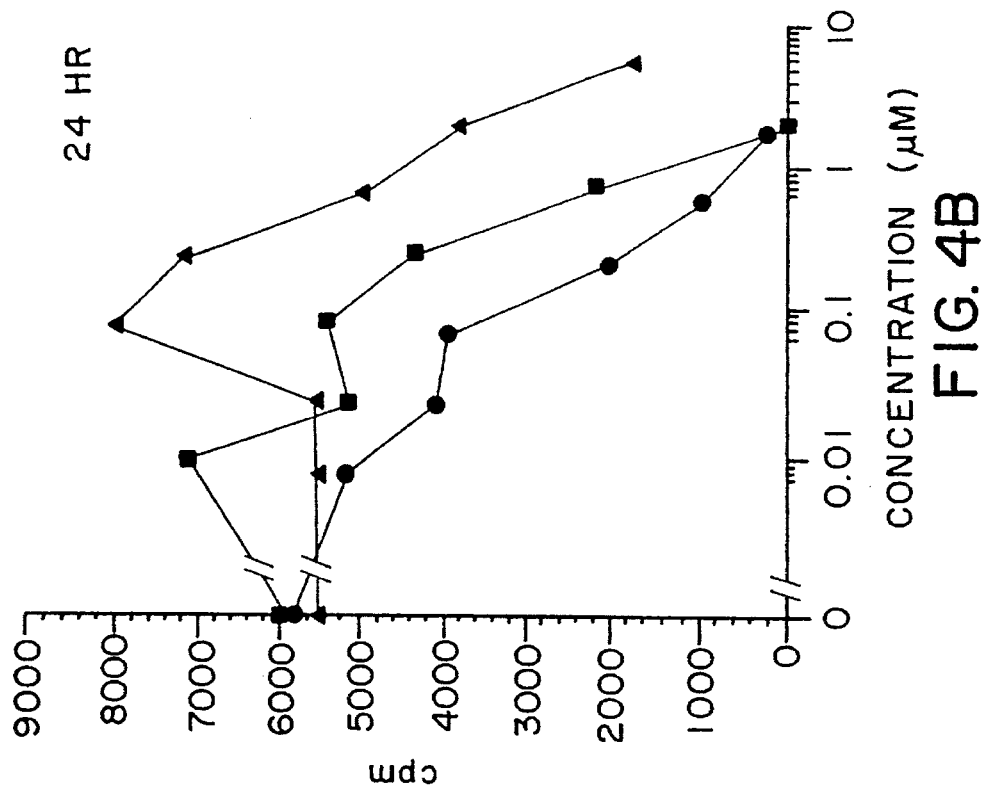
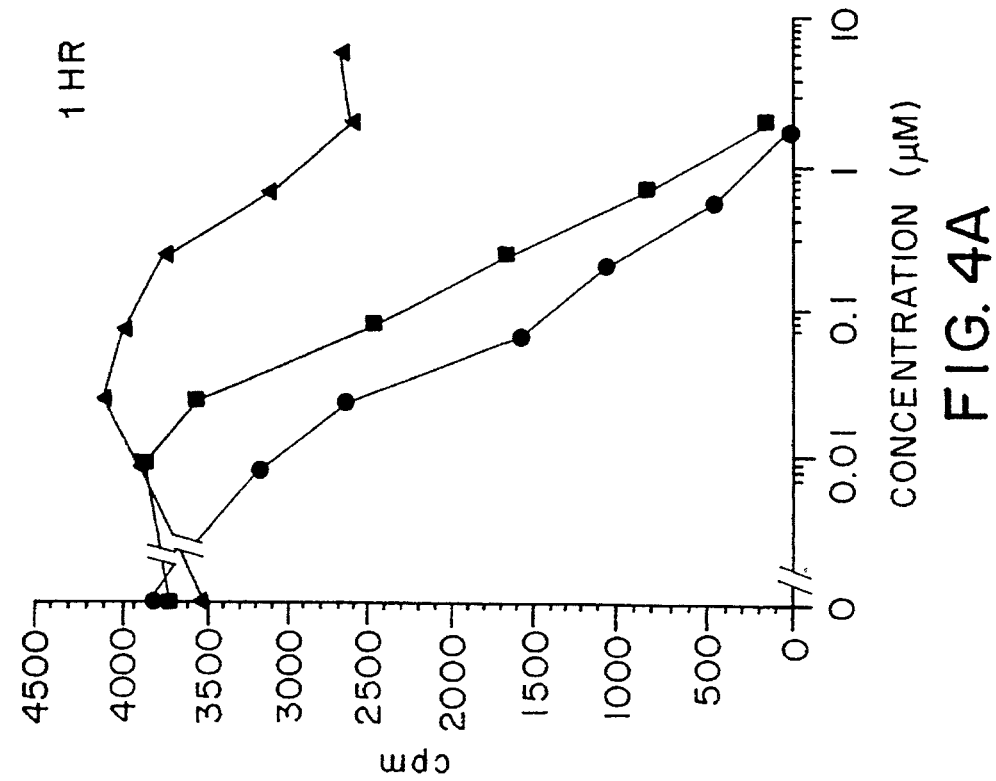

5,453,489

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 109 amino acids
        ( B ) TYPE: amino acid
        ( D ) TOPOLOGY: linear ( x i ) SEQUENCE DESCRIPTION: SEQ ID NO:1:

```
Asn Ala Pro Gln Pro Ser His Ile Ser Lys Tyr Ile Leu Arg Trp Arg
 1               5                  10                      15

Pro Lys Asn Ser Val Gly Arg Trp Lys Glu Ala Thr Ile Pro Gly His
                20              25                  30

Leu Asn Ser Tyr Thr Ile Lys Gly Leu Lys Pro Gly Val Val Tyr Glu
            35              40                  45

Gly Gln Leu Ile Ser Ile Gln Gln Tyr Gly His Gln Glu Val Thr Arg
        50              55                  60

Phe Asp Phe Thr Thr Thr Ser Thr Ser Thr Pro Val Thr Ser Asn Thr
65                      70                  75                  80

Val Thr Gly Glu Thr Thr Pro Phe Ser Pro Leu Val Ala Thr Ser Glu
                    85              90                  95
```

```
        Ser  Val  Thr  Glu  Ile  Thr  Ala  Ser  Ser  Phe  Val  Val  Ser
                       100                      105
```

( 2 ) INFORMATION FOR SEQ ID NO:2:

( i ) SEQUENCE CHARACTERISTICS:
        ( A ) LENGTH: 31 amino acids
        ( B ) TYPE: amino acid
        ( D ) TOPOLOGY: linear ( x i ) SEQUENCE DESCRIPTION: SEQ ID NO:2:

```
Asn  Ala  Pro  Gln  Pro  Ser  His  Ile  Ser  Lys  Tyr  Ile  Leu  Arg  Trp  Arg
1                   5                        10                           15

Pro  Lys  Asn  Ser  Val  Gly  Arg  Trp  Lys  Glu  Ala  Thr  Ile  Pro  Gly
               20                       25                      30
```

( 2 ) INFORMATION FOR SEQ ID NO:3:

( i ) SEQUENCE CHARACTERISTICS:
        ( A ) LENGTH: 31 amino acids
        ( B ) TYPE: amino acid
        ( D ) TOPOLOGY: linear ( x i ) SEQUENCE DESCRIPTION: SEQ ID NO:3:

```
Glu  Ala  Thr  Ile  Pro  Gly  His  Leu  Asn  Ser  Tyr  Thr  Ile  Lys  Gly  Leu
1                   5                        10                           15

Lys  Pro  Gly  Val  Val  Tyr  Glu  Gly  Gln  Leu  Ile  Ser  Ile  Gln  Gln
               20                       25                      30
```

( 2 ) INFORMATION FOR SEQ ID NO:4:

( i ) SEQUENCE CHARACTERISTICS:
        ( A ) LENGTH: 31 amino acids
        ( B ) TYPE: amino acid
        ( D ) TOPOLOGY: linear ( x i ) SEQUENCE DESCRIPTION: SEQ ID NO:4:

```
Leu  Ile  Ser  Ile  Gln  Gln  Tyr  Gly  His  Gln  Glu  Val  Thr  Arg  Phe  Asp
1                   5                        10                           15

Phe  Thr  Thr  Thr  Ser  Thr  Ser  Thr  Pro  Val  Thr  Ser  Asn  Thr  Val
               20                       25                      30
```

( 2 ) INFORMATION FOR SEQ ID NO:5:

( i ) SEQUENCE CHARACTERISTICS:
        ( A ) LENGTH: 34 amino acids
        ( B ) TYPE: amino acid
        ( D ) TOPOLOGY: linear ( x i ) SEQUENCE DESCRIPTION: SEQ ID NO:5:

```
Val  Thr  Ser  Asn  Thr  Val  Thr  Gly  Glu  Thr  Thr  Pro  Phe  Ser  Pro  Leu
1                   5                        10                           15

Val  Ala  Thr  Ser  Glu  Ser  Val  Thr  Glu  Ile  Thr  Ala  Ser  Ser  Phe  Val
               20                       25                      30

Val  Ser
```

( 2 ) INFORMATION FOR SEQ ID NO:6:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:6:

-continued

```
Asn Ala Pro Gln Pro Ser His Ile Ser Lys Tyr Ile Leu Arg Trp
 1           5                  10                        15
```

POLYPEPTIDE FRAGMENTS OF FIBRONECTIN WHICH CAN MODULATE EXTRACELLULAR MATRIX ASSEMBLY

This invention was made with Government support under Grant No. CA42507, and Cancer Center Support Grant No. CA30199, both awarded by the National Cancer Institute. The Government has certain rights in the invention.

FIELD OF THE INVENTION

The present invention relates to extracellular matrix assembly, and compounds involved in such processes. In a particular aspect, the present invention relates to methods to modulate assembly of extracellular matrix. In another aspect, the present invention relates to methods to isolate the extracellular matrix protein, fibronectin.

BACKGROUND OF THE INVENTION

As a constituent of the extracellular matrix, fibronectin is important for allowing cells to attach to the matrix. Fibronectin influences both the growth and migration of cells. Normal fibroblasts in tissue culture secrete fibronectin and assemble it into a matrix that is essential to their adhesion and growth. While many tumorigenic cells continue to produce fibronectin, they do not assemble the fibronectin into a matrix. This lack of matrix assembly is thought to contribute to the invasive properties of malignant cells. Thus, one important stage in the progression of cancer may be the transition from assembly to non-assembly of the extracellular matrix.

The general structure of fibronectin has been identified. The polypeptide is composed of a number of repeats, of which there are three kinds, type I, type II, and type III. The type I repeat is about 45 amino acids long and makes up the amino-terminal and carboxy-terminal ends of the polypeptide. Two 60 amino acid type II segments interrupt a row of nine type I repeats at the amino-terminus of fibronectin. Finally, 15–17 type III segments, each about 90 amino acids long, make up the middle of the polypeptide. Altogether, fibronectin contains nearly 2500 amino acid residues.

Matrix assembly requires the binding of fibronectin to cell surfaces followed by assembly into fibrils, and stabilization of the fibrils by disulfide cross-linking. Several regions within fibronectin are required for the assembly process. One such region is the amino terminal 29 kDa heparin binding domain. Cells have been shown to organize fibronectin fragments into fibrils only when heparin-binding fragments and an RGD-containing cell binding domain were present simultaneously [Woods et al., Exp. Cell Res. 177:272–283 (1988)]. The importance of the 29 kDa heparin-binding domain has been further underscored by the finding that recombinant fibronectin molecules lacking the 29 kDa region are not incorporated into extracellular matrix [Schwarzbauer, J. Cell Biol. 113:1463–1473 (1991)]. Moreover, molecules composed only of the 29 kDa region, plus the carboxy-terminal half of fibronectin were efficiently incorporated into the extracellular matrix. In view of the above information, the role of the 29 kDa region appears to be to mediate the binding of fibronectin to the cell surface.

Another region involved in matrix assembly is the RGD-containing cell binding domain of fibronectin. Monoclonal antibodies directed to the cell binding domain of fibronectin have been found to inhibit assembly of extracellular matrix [McDonald et al., J. Biol. Chem. 262:2957–2967 (1987)]. In addition, two monoclonal antibodies have been described that bind close to, but not directly to, the RGD site. These antibodies block the binding of cells to fibronectin and also block fibronectin matrix assembly [Nagai et al., J. Cell Biol. 114:1295–1305 (1991)].

The receptor that binds to the RGD site in fibronectin is, in most cells, the $\alpha_5\beta_1$ integrin [Pierschbacher and Ruoslahti, Nature 309:30–33 (1984)]. Accordingly, monoclonal antibodies directed against the $\alpha_5$ and $\beta_1$ integrin subunits have also been found to inhibit fibronectin matrix assembly, as well as the binding of fibronectin to matrix assembly sites. Conversely, overexpression of the $\alpha_5\beta_1$ integrin in CHO cells results in increased fibronectin matrix assembly. Taken together, these findings establish the importance of the interaction between fibronectin and the $\alpha_5\beta_1$ integrin during matrix assembly.

A third region of fibronectin has recently been shown to be involved in matrix assembly. A 56 kDa fragment from fibronectin, which contains the 40 kDa gelatin-binding domain, plus the first type III repeat has been found to inhibit the incorporation of exogenous fibronectin into the extracellular matrix [Chernousov et al., J. Biol. Chem. 266:10851–10858 (1991)]. In addition, monoclonal antibodies that bind within this 56 kDa region were also found to block fibronectin matrix assembly.

The identification of additional regions of fibronectin involved in the assembly of extracellular matrix will provide additional means to control the matrix assembly process. Such control is useful in many biologically and medically important situations, such as culturing cells, and directing tissue regeneration.

BRIEF DESCRIPTION OF THE INVENTION

In accordance with the present invention, we have developed a natural 14 kDa fragment and novel synthetic polypeptide(s) derived from the first type III repeat of fibronectin. The fragment and the synthetic polypeptide(s) of the invention encompass a fibronectin-fibronectin binding site, and are capable of inhibiting fibronectin matrix assembly. Moreover, the fragment and the synthetic polypeptide(s) of the invention, because they are capable of binding fibronectin, provide a new method for the isolation of fibronectin employing affinity chromatography.

BRIEF DESCRIPTION OF THE FIGURES

FIG. 4 shows the inhibition of fibronectin matrix assembly by the 14 kDa fragment, the kDa fragment, and fibronectin, after one hour (FIG. 4A) and after 24 hours (FIG. 4B)

FIG. 7A illustrates the inhibition of 14 kDa fragment-fibronectin binding.

FIG. 10 illustrates the effect of added polypeptides on endogenous fibronectin matrix assembly by the addition of polypeptides, wherein FIG 10A shows the control, FIG. 10B shows the addition of the 70 kDA fragment, FIG. 10C shows the addition of the P1 polypeptide, and FIG. 10D shows the addition of the P2 polypeptide.

DETAILED DESCRIPTION OF THE INVENTION

Figure 1:
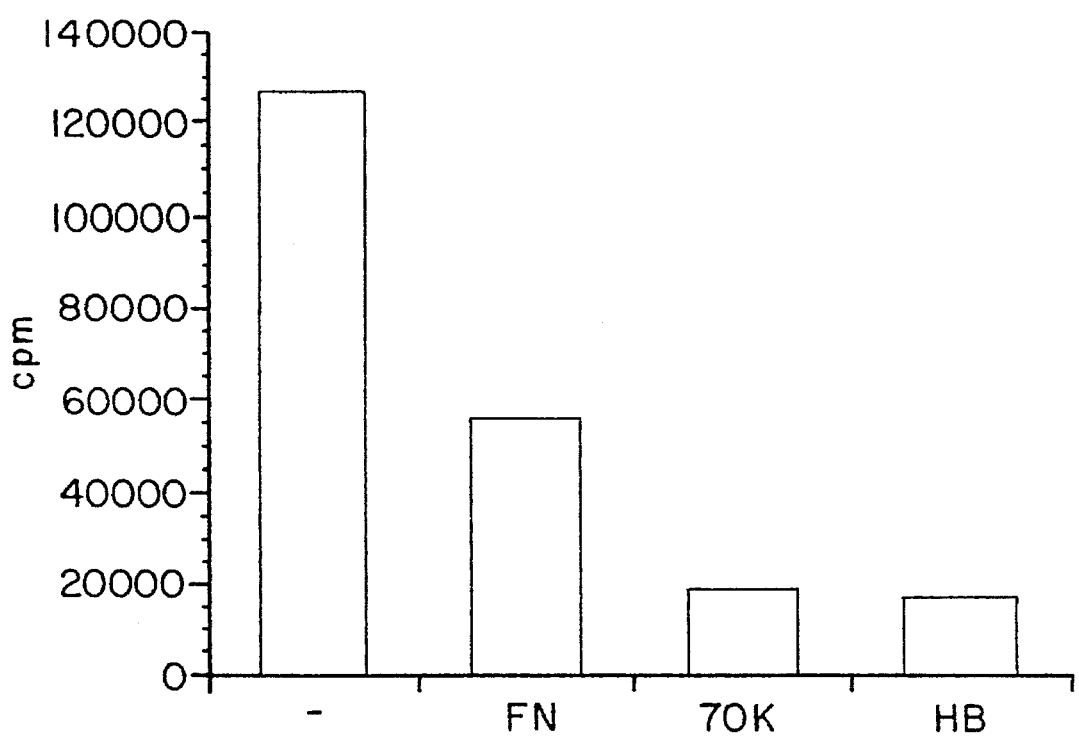
FIG. 1 illustrates the inhibition of fibronectin matrix assembly by fibronectin, 70 kDa fragment, and heparin binding fragments of fibronectin.

In accordance with the present invention, there are provided novel polypeptide(s) characterized by:

having a molecular weight of about 14 kDa, having the ability to bind fibronectin directly, and substantially reducing fibronectin matrix assembly, while not reducing substantially the ability of fibronectin to bind to cells, or functional fragments thereof, or multimeric forms of said polypeptide or functional fragments thereof.

The polypeptides of the invention can be further characterized as being capable of inhibiting fibronectin-fibronectin association. The polypeptides of the invention can be still further characterized as binding specifically to IMR-90 cells, but not to HT-1080 cells. The invention polypeptides can be even further characterized by being substantially more effective for binding to fibronectin than is fibronectin itself. The 14 kDa polypeptide of the invention can also be characterized as essentially encompassing the first type III repeat unit of fibronectin.

Exemplary polypeptide(s) contemplated by the present invention include those which have substantially the same amino acid sequence as set forth in Sequence ID No. 1. As used herein, the term "substantially" refers to those sequences which have insignificant differences, relative to the sequence set forth in Sequence ID No. 1. For example, changes of amino acids that do not abolish the fibronectin-binding properties of the polypeptide, or fragments thereof, of the present invention, are contemplated to be within the scope of the present invention. In addition, homologous polypeptides from different species (which are not likely to significantly differ from the above-described sequence) are also contemplated to be within the scope of the present invention, as well as allelic variations within the same species.

Also included in the scope of the present invention are functional fragments of the above described polypeptide. As used herein, the term "functional fragments thereof" refers to sequences which contain less than all of the residues set forth in Sequence ID No. 1, yet retain at least a portion of the functional activity thereof.

Examples of functional fragments include polypeptides having the amino acid sequence:

NAPQPSHISK YILRWRPKNS VGRWKEATIP G (P1; Sequence ID No. 2) or

EATIPGHLNS YTIKGLKPGV VYEGQLISIQ Q (P2; Sequence ID No. 3) or

LISIQQYGHQ EVTRFDFTTT STSTPVTSNT V (P3; Sequence ID No. 4) or

VTSNTVTGET TPFSPLVATS ESVTEITASS FVVS (P4; Sequence ID No. 5), or functional fragments thereof. Additionally, combinations comprising at least two of the polypeptides P1–P4, as well as combinations comprising fragments of at least two of the polypeptides P1-P4 are also contemplated.

Polypeptides contemplated by the present invention can be derived from fibronectin in any of a variety of ways, such as, for example, by proteolytic cleavage thereof, and the like. Alternatively, invention polypeptides can be produced by recombinant means, by chemical synthesis, and the like.

In accordance with another embodiment of the present invention, there are provided antibodies raised against the polypeptides described above, as well as antibody-like proteins (i.e., recombinant antibodies, single-chain antibodies, and the like), recombinant protein fragments and RNA sequences that specifically bind the above-described polypeptides. One skilled in the art can readily prepare such binding molecules, without undue experimentation, given the sequence and description of the 14 kDa polypeptide and functional fragments thereof described herein.

In accordance with still another embodiment of the present invention, there is provided a method to inhibit the ability of fibronectin to participate in extracellular matrix assembly, said method comprising blocking fibronectin-fibronectin binding. Such blocking can be accomplished in a variety of ways, for example, by contacting the cells or tissues to be treated with an effective amount of the invention polypeptide.

The ability to inhibit the formation of extracellular matrix is of great benefit, for example, in the prevention of unwanted extracellular matrix accumulation, as occurs in scar formation.

In accordance with yet another embodiment of the present invention, there is provided a method to inhibit, in a cellular system, the ability of a fibronectin molecule to bind to another fibronectin molecule, said method comprising administering to said system an effective amount of the invention polypeptide, as described above, an antibody thereto, or a polypeptide containing the cognate polypeptide binding site.

Polypeptides contemplated for use in this method include polypeptides P1–P4, as described above, or functional fragments thereof. A presently preferred polypeptide for use in this embodiment of the invention has the amino acid sequence P1, as described above. In addition, combinations of at least two of the polypeptides P1–P4, or combinations of fragments of at least two of the polypeptides P1–P4 are also contemplated.

Those of skill in the art can readily identify suitable modes of administration of the compositions of the invention (e.g., said polypeptide, antibody, RNA, and the like), such as, for example, by injection (e.g., IP, subcutaneous), local application (e.g., topical application to a surface wound), gradual infusion (e.g., via osmotic pump), and the like.

Since the invention polypeptides bind fibronectin ( for example, from plasma), they can be used to coat biological and medical materials (such as, for example implants) so that the materials bind fibronectin from biological fluid, and thereby become adhesive to cells, thereby enhancing the biocompatibility of such materials.

In accordance with a still further embodiment of the present invention, there is provided a method to promote, in a cellular system, assembly of extracellular matrix, said method comprising contacting said system with an effective amount of invention polypeptide, as described above. Alternatively, antibodies that bind to any one or more of the invention polypeptides can be used to nucleate fibronectin fibril formation, and thereby promote matrix assembly.

Presently preferred polypeptides for use in this embodiment of the invention are polypeptide P1 and P4, as described above. Thus, the P4 polypeptide of the present invention, at elevated concentrations, promotes matrix assembly. This is possibly the result of the formation of aggregates of P4. This function of P4 can likely be reproduced using polypeptides having multiple, tandem sequences of the P4 polypeptide, since such a species would mimic an aggregate of monomers. Alternatively, the polypeptide P1, which has been shown to form aggregates, and thereby increase the deposition of fibronectin to a solid surface, can be used to promote the assembly of extracellular matrix.

It is envisioned that all of the polypeptides of the invention which can be used to inhibit (or prevent) matrix assembly can be targeted to the extracellular matrix by incorporating other matrix binding sites therein. Other matrix binding sites include, for example, a heparin-binding site, an RGD-binding site, and the like.

The invention polypeptides could target materials to tissues that contain fibronectin. This is accomplished by coupling the 14 kDa fragment of the invention (see Sequence ID No. 1) or polypeptide P1 (see Sequence ID No. 2) or functional fragments thereof, with a molecule which is desired to be targetted to fibronectin-containing tissues or cells, and contacting the tissues or cells with the coupled molecules.

In accordance with yet another embodiment of the present invention, there is provided a method to decrease tumorigenicity of a cell, said method comprising promoting the formation of fibronectin extracellular matrix by contacting the matrix surrounding said cell with an effective amount of invention polypeptide, or antibody to said polypeptide (or functional fragment thereof), or a peptide containing the cognate peptide binding site for fibronectin.

Also contemplated within the scope of the present invention is a method to enhance wound healing in a subject, said method comprising administering to said subject an amount of invention polypeptide (or antibodies thereto) effective to enhance cell migration into the wound site.

In accordance with still another embodiment of the present invention, there is provided a method to prevent scar formation in a subject as a result of the healing of a wound, said method comprising administering to said subject an effective amount of invention polypeptide (or antibodies thereto) so as to prevent excessive matrix formation (which, in turn prevents scar formation).

In accordance with another embodiment of the present invention, there is provided a method of promoting cell attachment to a surface, said method comprising:

contacting cells with a fibronectin-treated surface, wherein said fibronectin-treated surface has been coated with the 14 kDa fragment set forth in Sequence ID No. 1 and/or polypeptide P1 set forth in Sequence ID No. 2, or functional fragments thereof, with a fibronectin-containing solution under conditions allowing fibronectin to bind to said surface, thereby producing a fibronectin-treated surface, and thereafter contacting cells with said fibronectin-treated surface.

In accordance with still another embodiment of the present invention, there is provided a method of isolating fibronectin from a mixture of proteins, said method comprising:

subjecting said mixture to affinity chromatography conditions employing a support containing at least one of the 14 kDa fragment set forth in Sequence ID No. 1 or polypeptide P1 set forth in Sequence ID No. 2, and eluting the retained fibronectin from said support.

In accordance with yet another embodiment of the present invention, there are provided aggregates and synthetic oligomers of the invention polypeptide. Such forms of the invention polypeptide are capable of binding fibronectin and nucleating the assembly of matrix.

In accordance with still another embodiment of the present invention, there is provided a method to isolate fibronectin from solutions containing same, by contacting such solutions with an affinity support having bound thereto a polypeptide of the invention, or a fragment thereof.

In accordance with a still further embodiment of the present invention, there is provided a method to remove fibronectin from solutions containing same, by contacting such solutions with an affinity support having bound thereto a polypeptide of the invention, or a fragment thereof.

The invention will now be described in greater detail by reference to the following non-limiting examples.

EXAMPLES

Example I

Peptides, Antibodies and cell lines

Alpha-Minimal Essential Medium ($\alpha$-MEM) was purchased from Gibco Laboratories (Grand Island, N.Y.), Fetal Calf Serum (FCS) from Tissue Culture Biologicals (Tulare, Calif.), and Glutamine Pen-Strep from Irvine Scientific (Santa Ana, Calif.). Immulon 2 Removawell strips were obtained from Dynatech Laboratories (Chantilly, Va.). Iodo-Gen was purchased from Pierce (Rockford, Ill.). CNBr-activated Sepharose, heparin-Sepharose and Gelatin-Sepharose were obtained from Pharmacia LKB (Piscataway, N.J.). Precast SDS-PAGE gels were purchased from BioRad (Richmond, Calif.) and Novex (San Diego, Calif.). Lab-Tek 8-well Chamber Slides were obtained from Nunc (Naperville, Ill.). HPLC columns were purchased from Vydac (Hesperia, Calif.). Collagen type I was obtained from Collaborative Research (Bedford, Mass.). All other reagents were acquired from Sigma (St. Louis, Mo.).

IMR-90 (ATCC No. CCL-186) and HT-1080 (ATCC NO. CCL-121) cells were cultured in $\alpha$-MEM supplemented with 10% heat-inactivated FCS and Glutamine Pen-Strep. IMR-90 cells used for experiments were between passage number 11 and 20, cells in later passages were not used.

Human fibronectin is commercially available, and was obtained from the Blood Transfusion Service of the Finnish Red Cross in Helsinki. To prepare the heparin-binding fragments, fibronectin was digested with $\alpha$-chymotrypsin (0.1% by weight, TLCK treated) for 4 hours at 25° C. The digestion was stopped by adding phenylmethylsulphonyl fluoride (20 µg/ml final concentration) and the preparation was passed over a gelatin-Sepharose column [Engvall and Ruoslahti, Int. J. Cancer 20:1–5 (1977)]. After washing the gelatin-Sepharose column with phosphate-buffered saline (PBS), gelatin bound material was eluted with 8M urea, 50 mM Tris-HCl, pH 7.5, followed by extensive dialysis against distilled water and lyophilization. The flow through from the gelatin-Sepharose column was collected and passed over a heparin-Sepharose column. The heparin-Sepharose column was washed with PBS, then heparin bound fibronectin fragments were eluted with 1M NaCl, 50mMTris-HCl, pH 7.5, then dialyzed against distilled water and lyophilized.

The amino terminal 70 kDa fragment was produced as previously described by McKeown-Longo and Mosher, J. Cell Biol. 100:364–374 (1985). The 14 kDa fragment was purified from heparin-binding fragments by reverse phase HPLC on a C-4 column. After applying heparin-binding fragments to the HPLC column in 0.06% trifluoroacetic acid, the column was eluted with a linear gradient of 0 to 60% acetonitrile in 0.06% trifluoroacetic acid. The 14 kDa fragment was eluted in the 45% acetonitrile fractions.

Polypeptides representing various regions of the above-described 14 kDa fragment of fibronectin were synthesized at the Protein Chemistry Laboratory at the La Jolla Cancer Research Foundation. All polypeptides used in experiments were purified by reverse phase HPLC. Polypeptide P1 (Sequence ID No. 2; sequence: NAPQPSHISK YILRWR-PKNS VGRWKEATIP G) represents the region from amino acids 600–630; polypeptide P2 (Sequence ID No. 3; sequence: EATIPGHLNS YTIKGLKPGV VYEGQLISIQ Q) represents the region from amino acids 625–656; polypeptide P3 (Sequence ID No. 4; sequence: LISIQQYGHQE VTRFDFTTT STSTPVTSNT V) represents the region from amino acids 650–680; and polypeptide P4 (Sequence ID No. 5; sequence: VTSNTVTGET TPFS-PLVATS ESVTEITASS FVVS) represents the region from amino acids 675–708 of the mature protein according to the numbering method of Kornblihtt et al., EMBO J. 4:1755–1759 (1985).

Proteins (20–100 µg of protein in 0.1 ml, 50 mM $KPO_4$, pH 7.5) were iodinated by using Iodo-Gen as previously described (Fraker and Speck, 1978). Typical values for specific activity were $10^9$ µCi/mmole for fibronectin, $5\times10^8$ µCi/mmole for 70 kDa, $5\times10^8$ µCi/mmole for 14 kDa, and 0.5 µCi/µg for heparin-binding fragments.

Example II

Assays

Matrix assembly assays were performed by using $^{125}$I-fibronectin, essentially as described previously (McKeown-Longo and Mosher, J. Cell Biol. 97:466–472 (1983); McKeown-Longo and Mosher (1985), supra). Prior to labeling, cells were grown to confluence in 96-well dishes in α-MEM+10% FCS. Cells were labeled in α-MEM+10% fibronectin-deficient FCS plus 5 µCi/ml of $^{125}$I-fibronectin. Fibronectin-deficient FCS was prepared by passing FCS over a gelatin-Sepharose column to remove fibronectin [Engvall and Ruoslahti, Int. J. Cancer 20:1–5 (1977)]. The concentration of unlabeled fibronectin in α-MEM+10% fibronectin-deficient FCS was approximately 0.2 µg/ml as determined by ELISA using anti-bovine fibronectin antibodies. Where indicated, cells were labeled in the presence of excess non-radioactive competitor proteins such as fibronectin, or the 70 kDa fragment, or polypeptides P1–P4. Cells that were labeled for 1 hour were washed four times with ice-cold PBS, then lysed in 1N NaOH and cell-bound radioactivity was measured in the NaOH soluble fraction. Cells that were labeled with $^{125}$I-heparin-binding fragments were also washed with PBS, then cells were solubilized with SDS-PAGE sample buffer (2% SDS, 67 mM Tris-HCl, pH 6.8, 10% glycerol, 0.03% bromophenol blue) and proteins were separated on BioRad 4–20% Ready Gels, followed by autoradiography. Cells that were labeled with $^{125}$I-fibronectin for 24 hours were washed as described above, then either lysed directly in 4% SDS, 25 mM Tris-HCl, pH 7.5, for a measure of total 125I-fibronectin, or proteins were separated into 1% deoxycholate soluble and insoluble pools (pools I and II) as described by McKeown-Longo and Mosher (1985), supra. The data presented in FIGS. 4 and 9 (described in greater detail below) depict only specific $^{125}$I-fibronectin binding. Specific binding was defined as that amount of binding which was competed by 2 µM unlabeled fibronectin, and was typically 60–70% of the total $^{125}$I-fibronectin binding.

Protein-protein binding assays were performed on Immulon 2, Removawell strips. Proteins were coated onto wells in 100 mM $Na_2CO_3$, pH 9.5, in a moist chamber at 4° C. over night. The wells were washed three times with PBS followed by blocking with 0.2% bovine serum albumin in PBS (0.2% BSA) at 37° C. for 1 hour. Radiolabeled proteins were added to the wells in 0.2% BSA at 5µCi/ml. Proteins were allowed to bind for 2 hours at 37° C., then the wells were washed four times with 0.2% BSA, the wells were removed and the bound $^{125}$I was measured.

Polypeptides were coupled to CNBr-activated Sepharose CL-4B according to the manufacturer's recommendations. The concentration of polypeptide was typically 8–10 mg polypeptide/ml of resin. Three ml of human plasma was passed over one ml columns of polypeptide P1, polypeptide P2, or gelatin-Sepharose as a positive control, or plain Sepharose as a negative control. The flow-through fractions were collected and the columns were washed with 20 column volumes of PBS+5 mM EDTA (PBS/EDTA), followed by 3 column volumes of 0.2M NaCl in PBS/EDTA. Bound proteins were then eluted with 2 volumes of 8M urea in PBS/EDTA, the eluates were collected in two, 1-volume fractions. Equal volumes of each fraction were analyzed by SDS-PAGE on Novex 4–12% Tris-Glycine gels, proteins were visualized by staining with coomassie blue. The 0.2M NaCl in PBS/EDTA washes contained no significant amounts of protein and are therefore not shown in FIG. 8.

IMR-90 cells were seeded onto Lab-Tek 8 well Chamber Slides. Wells were precoated with 50 µg/ml collagen type I to enhance the attachment of cells to the wells. Cells were allowed to attach and spread for one hour at 37° C., followed by washing once with α-MEM+10% fibronectin-deficient FCS, and incubation in this medium plus either no additions, addition of the 70 kDa fibronectin fragment, or addition of polypeptides as described below (see discussion related to data presented in FIG. 10). At the appropriate time cells were fixed with 3.7% paraformaldehyde, 60 mM sucrose, in PBS, pH 7.4 for 30 minutes at room temperature. Cell layers were washed three times with 0.2% BSA in PBS, then stained with 10 µg/ml of affinity-purified, rhodamine-labeled rabbit anti-human fibronectin antibodies.

EXAMPLE III

Identification of novel fibronectin fragments

To identify new fibronectin fragments that would define sites important for matrix assembly, fibronectin was digested with chymotrypsin and the preparation was separated into heparin binding and gelatin binding fragments. The fragment preparations were then tested for their ability to inhibit fibronectin matrix assembly by using $^{125}$I-fibronectin and IMR-90 cells, as described by McKeown-Longo and Mosher (1985), supra. As shown previously, unlabeled fibronectin and an amino terminal 70 kDa cathepsin-D fibronectin fragment inhibited matrix assembly in this assay (McKeown-Longo and Mosher (1985), supra; and FIG. 1). Among the chymotryptic fragments, the heparin-binding fragments inhibited matrix assembly (FIG. 1), whereas, the gelatin binding fragments had little effect.

The experiments summarized in FIG. 1 were carried out as follows: Confluent monolayers of IMR-90 cells were incubated for 24 hours at 37° C. with $^{125}$I-fibronectin in the presence or absence of unlabeled fibronectin (250 µg/ml), 70 kDa (70 µg/ml), or heparin-binding fragments (1 mg/ml). Cells were washed with PBS, then extracted into deoxycholate soluble and insoluble pools as described above in EXAMPLE I. The columns represent the amount of $^{125}$I-fibronectin extracted in the deoxycholate insoluble pool. All values are averages of duplicate determinations. Cells were incubated with either no competitor (−), or fibronectin (FN), 70 kDa (70K), or heparin-binding fragments (HB) as competitors of $^{125}$I-fibronectin.

To determine which fragments in the heparin-binding fragment preparation were responsible for inhibiting matrix assembly, $^{125}$I-labeled heparin-binding fragments were incubated with cell monolayers. The fragments that bound to the cells were extracted and analyzed on SDS-PAGE.

Figure 2:
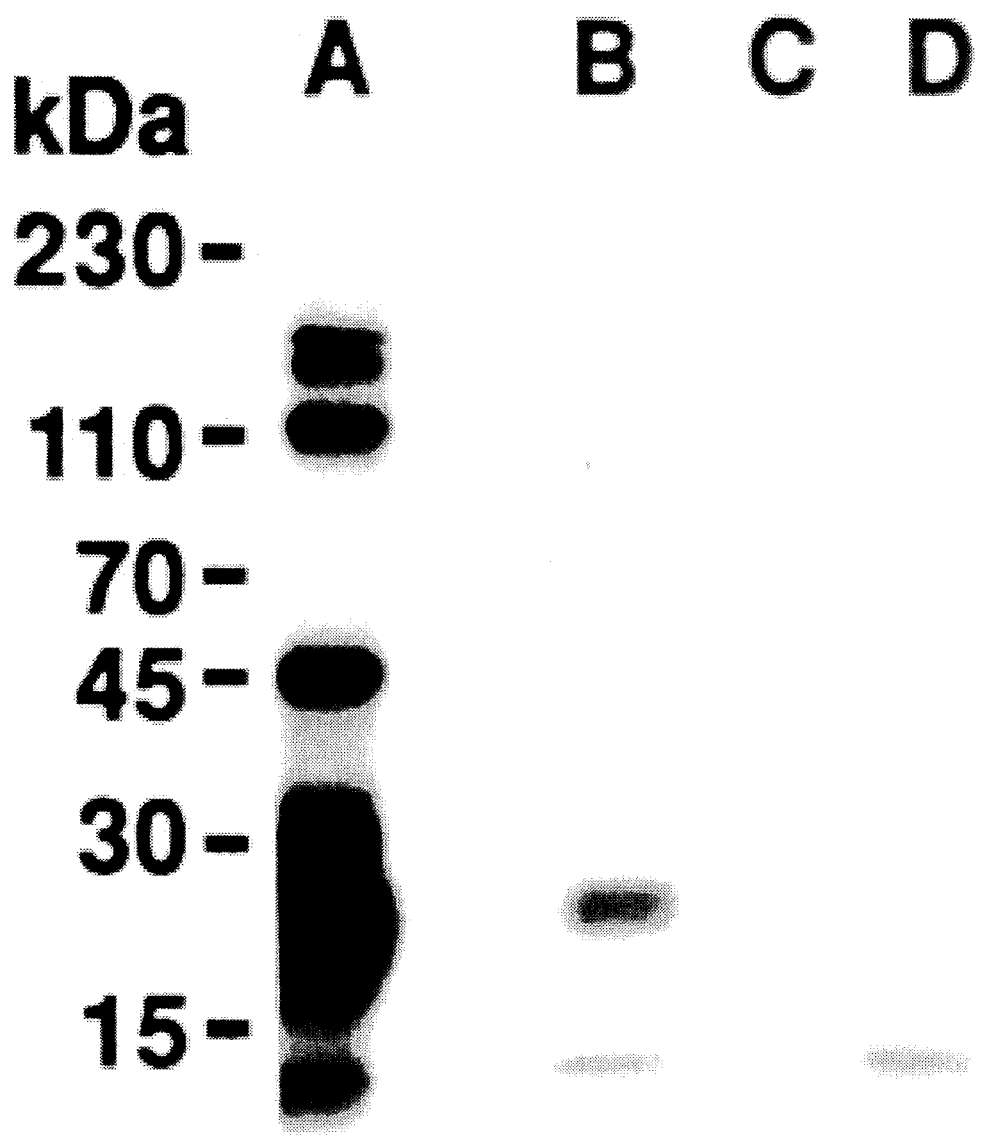
FIG. 2 illustrates the binding of 29 kDa and 14 kDa fragments to IMR-90 Cells.

IMR-90 cells were incubated for one hour at 37° C. with $^{125}$I-labeled heparin-binding fragments (2 µCi/ml) in the presence or absence of unlabelled heparin-binding fragments (250 µg/ml), or 70 kDa (1 µM). Cells were then washed with PBS and harvested for analysis by SDS-PAGE as described above. In lane A of FIG. 2, a sample of the $^{125}$I-labeled heparin-binding fragment starting material; lane B of FIG. 2 shows fragments that bound in the absence of competition; lane C of FIG. 2 shows fragments bound in the presence of unlabeled heparin-binding fragments; lane D of FIG. 2 shows fragments bound in the presence of unlabeled 70 kDa. The positions of molecular mass standards are indicated to the left of the gel.

Although the heparin-binding fragment preparation contains many polypeptides, ranging from 12 to 200 kDa, only two of these fragments, a 29 kDa fragment and 14 kDa fragment, bound to IMR-90 cells (FIG. 2, lane B). The binding of both fragments was shown to be specific by competition with excess unlabeled heparin-binding fragments (FIG. 2, lanes B and C). Since 29 kDa is the size of the amino terminal heparin binding domain, it was possible that the 29 kDa fragment observed binding to cells in this experiment represented that amino terminal fragment. To test this, cells were incubated with $^{125}$I-labeled heparin-binding fragments in the presence of excess unlabeled amino terminal 70 kDa fragment. The unlabeled 70 kDa fragment competed for the 29 kDa heparin-binding fragment, indicating that this fragment did represent the amino terminal heparin binding domain (FIG. 2, lane D). Interestingly, the 70 kDa fragment did not compete for the 14 kDa heparin-binding fragment (FIG. 2, lane D), suggesting that the 14 kDa region is not represented in the 70 kDa fragment. Thus, the 29 kDa fragment represents the amino terminal heparin binding region, while the 14 kDa fragment apparently lies somewhere outside the amino terminal 70 kDa region.

The 29 kDa amino terminal fragment has been shown to inhibit matrix assembly [see, for example, McKeown-Longo and Mosher (1985), supra; McDonald et al., J. Biol. Chem. 262:2957–2967 (1987); Quade and McDonald, J. Biol. Chem. 263:19602–19609 (1988)]. It was not clear, therefore, whether the inhibition of matrix assembly caused by heparin-binding fragments was due solely to the 29 kDa fragment, or whether the 14 kDa fragment shared such activity.

Figure 3A:
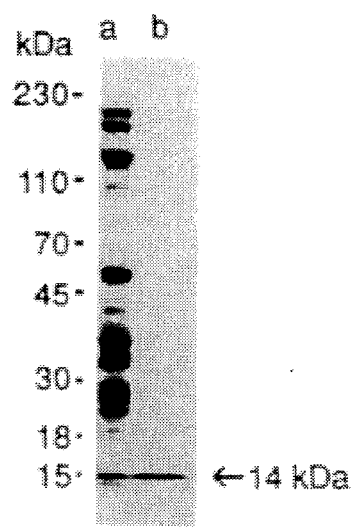
FIG. 3A illustrates the purification of the 14 kDa fibronectin fragment and FIG. 3B illustrates its location in fibronectin.
Figure 3B:
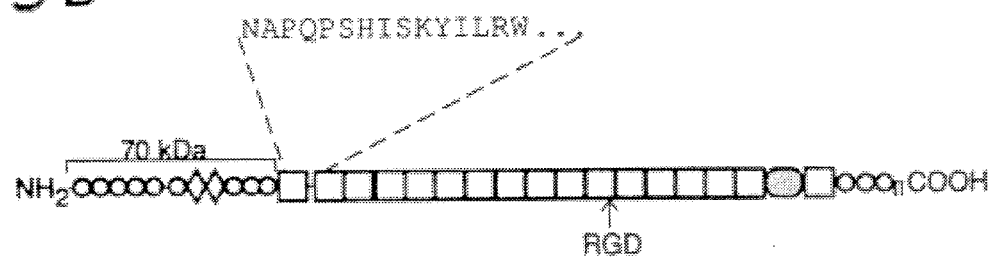

To test this, the 14 kDa fragment was purified to homogeneity by using reverse phase HPLC (FIG. 3A, lane b). Panel A of FIG. 3 shows SDS-PAGE analysis of the heparin-binding fragment starting material (lane a), and the purified 14 kDa preparation (lane b). The gel was stained with coomassie blue. The positions of molecular mass standards are indicated to the left of the gel. The position of the 14 kDa fragment is indicated to the right of the gel. Panel B of FIG. 3 shows a diagram of fibronectin, outlining the locations of the 14 kDa fragment and the various other fragments relevant to the present invention. The three repeating units of fibronectin are depicted as follows; type I repeats, circles; type II repeats, diamonds; type III repeats, squares. The CS1 region is depicted by a shaded oval. The amino terminal sequence of the 14 kDa fragment is shown with dashed lines extending to the location on the diagram representing the area covered by the 14 kDa fragment.

Amino acid sequencing of the 14 kDa fragment yielded the following amino terminal sequence: NAPQPSHISKY-ILRW (SEQ ID NO:6). This sequence corresponds to a region just past the beginning of the first fibronectin type III repeat (see FIG. 3B), starting at amino acid residue 600 of the mature protein (according to the numbering of Kornblihtt et al. (1985), supra. Judging from the size of the fragment, it is likely to encompass a sequence that extends partially into the second type III repeat.

Example IV

Functional activities of novel fibronectin fragments

Binding of the 14 kDa fragment to cells was tested by using IMR-90 cells, which construct an extensive fibronectin matrix, and HT-1080 cells, which produce no matrix. Cells were incubated with purified $^{125}$I-14 kDa in the presence or absence of unlabeled heparin-binding fragments or purified 14 kDa fragment. Approximately 50–60% of the $^{125}$I-14 kDa fragment that bound to IMR-90 cells was competed by unlabeled heparin-binding fragments or 14 kDa fragment. However binding to HT-1080 cells was only at the level of non-specific binding to IMR-90 cells, and none of the $^{125}$I-14 kDa that bound to HT-1080 cells was competed by unlabeled heparin-binding fragments. These data indicate that the 14 kDa fragment binds specifically to IMR-90 cells but not to HT-1080 cells.

The purified 14 kDa fragment was tested for its ability to inhibit matrix assembly. IMR-90 cells were incubated with $^{125}$I-fibronectin in various concentrations of excess unlabeled fibronectin 70 kDa fragment or 14 kDa fragment. Cells were labeled for either 1 hour to assay for fibronectin binding to cell surfaces, or 24 hours to assay for fibronectin incorporation into the extracellular matrix.

With reference to FIG. 4, confluent monolayers of IMR-90 cells were labeled with $^{125}$I-fibronectin in the presence of various concentrations of unlabeled fibronectin (■), 70 kDa (●) or 14 kDa (▲). In panel A, cells were labeled for one hour, washed, and the total radioactivity bound was measured. In panel B, cells were labeled for 24 hours and the amount of $^{125}$I-fibronectin in the deoxycholate insoluble pool was measured. Each data point is the average of duplicate determinations.

Both fibronectin and the 70 kDa fragment completely inhibited the binding of $^{125}$I-fibronectin to cells, but the 14 kDa fragment only partially reduced the amount of $^{125}$I-fibronectin bound to cells (FIG. 4A). The 14 kDa fragment had a much more pronounced effect on the amount of fibronectin incorporated into the extracellular matrix after 24 hours of incubation with $^{125}$I-fibronectin. As shown in FIG. 4B, the 14 kDa fragment inhibited fibronectin matrix assembly by approximately 70% (at 5 μM, the highest concentration tested). The IC$_{50}$ of the 14 kDa fragment was between 1–2 μM, which was 5–10 fold higher than that of fibronectin or the 70 kDa fragment. Thus, the purified 14 kDa fragment inhibited fibronectin matrix assembly in this assay, and the inhibitory effect seen with heparin-binding fragments was likely due to a combination of the effects of both the 29 kDa and the 14 kDa fragments.

Example V

Mechanistic studies

To examine the mechanism by which the 14 kDa fragment inhibits matrix assembly, the ability of this fragment to interact with fibronectin was tested. Fibronectin was coated onto plastic wells in concentrations ranging from 0–100 μg/ml, blocked with BSA, then the wells were probed with $^{125}$I-labeled 14 kDa fragment (panel A) or $^{125}$I-labeled fibronectin (panel B) for 2 hours at 37° C.. The amount of radioiodinated protein bound was measured after washing extensively with 0.2% BSA in PBS. Each data point is the average of duplicate determinations.

Figure 5A:
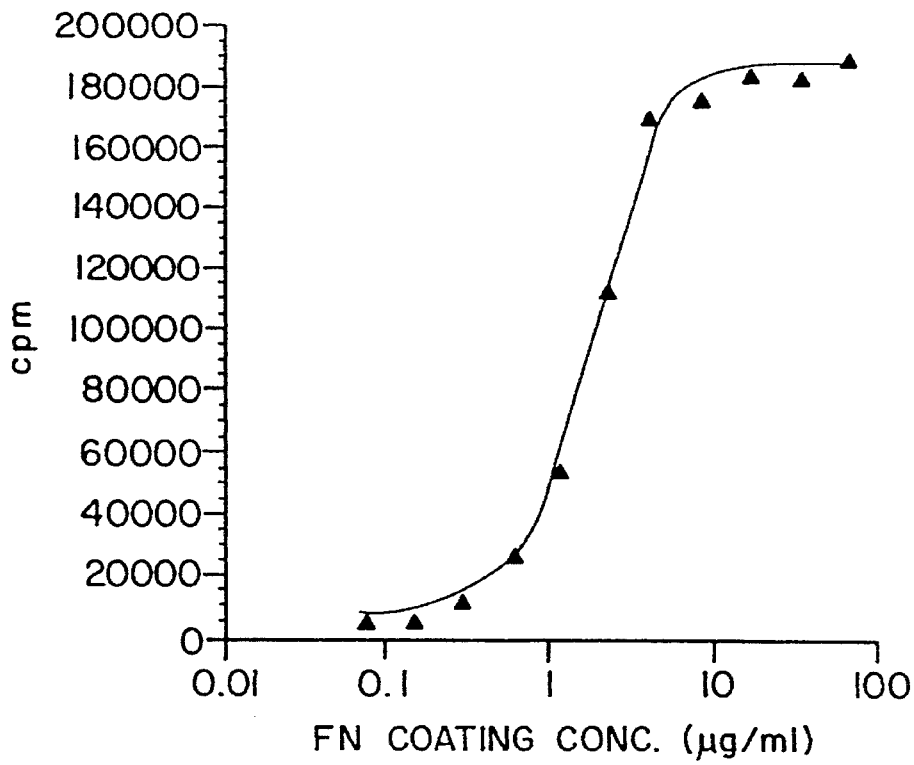
FIG. 5A illustrates binding of the 14 kDa fragment to fibronectin and FIG. 5B illustrates the binding of fibronectin to fibronectin.
Figure 5B:
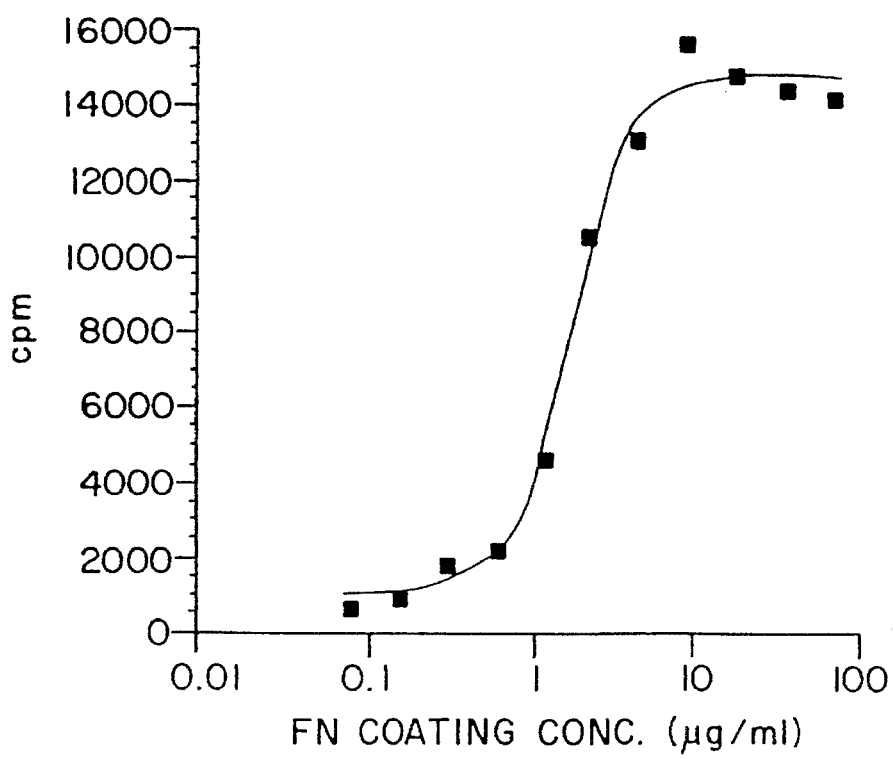

As shown in FIGS. 5A and B, $^{125}$I-fibronectin and $^{125}$I-14 kDa fragment both bound to fibronectin coated on the plastic in a dose dependent manner. The total $^{125}$I-14 kDa bound was approximately 10 fold higher than the total amount of $^{125}$I-fibronectin bound [compare FIG. 5A (14 kDa fragment) to 5B (full-length fibronectin)]. Taking into account the specific activities and the amounts of each protein added, this indicated that the maximal binding of the 14 kDa fragment to fibronectin was 5–10 fold more efficient (on a molar basis) than fibronectin binding to fibronectin.

The ability of the 14 kDa fragment to compete for fibronectin-fibronectin binding was then tested as follows. Plastic wells were coated with 5 μg/ml fibronectin, blocked with BSA, then probed with $^{125}$I-14 kDa (FIG. 6A), or $^{125}$I-fibronectin (FIG. 6B), in the presence of various concentrations of unlabeled 14 kDa (▲) or fibronectin (■). The solutions were incubated for 2 hours at 37° C., followed by extensive washing with 0.2% BSA in PBS, and measurement of the radioactivity bound to the wells. Each data point is the average of duplicate determinations.

Figure 6A:
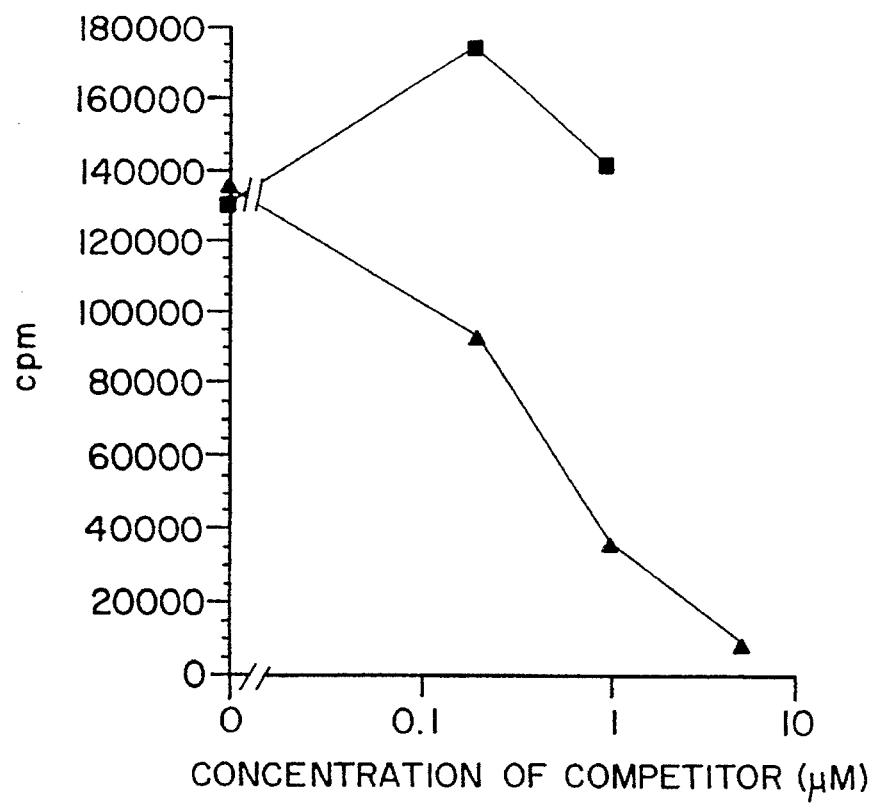
FIG. 6 illustrates the inhibition of fibronectin-fibronectin and 14 kDa-fibronectin binding binding by the 14 kDa fragment by the 14 kDa fragment (FIG. 6A) and by fibronectin (FIG. 6B).

As seen in FIGS. 6A and B, the unlabeled 14 kDa fragment competed efficiently for the binding of $^{125}$I-14 kDa fragment to fibronectin, thereby demonstrating the specificity of this binding (FIG. 6A). Yet, unlabeled fibronectin did not compete for the binding of $^{125}$I-14 kDa fragment to fibronectin. One explanation for this is that the unlabeled fibronectin is binding to the fibronectin coating, and that $^{125}$-14 kDa fragment then binds to either the coated or the adsorbed fibronectin.

Figure 6B:
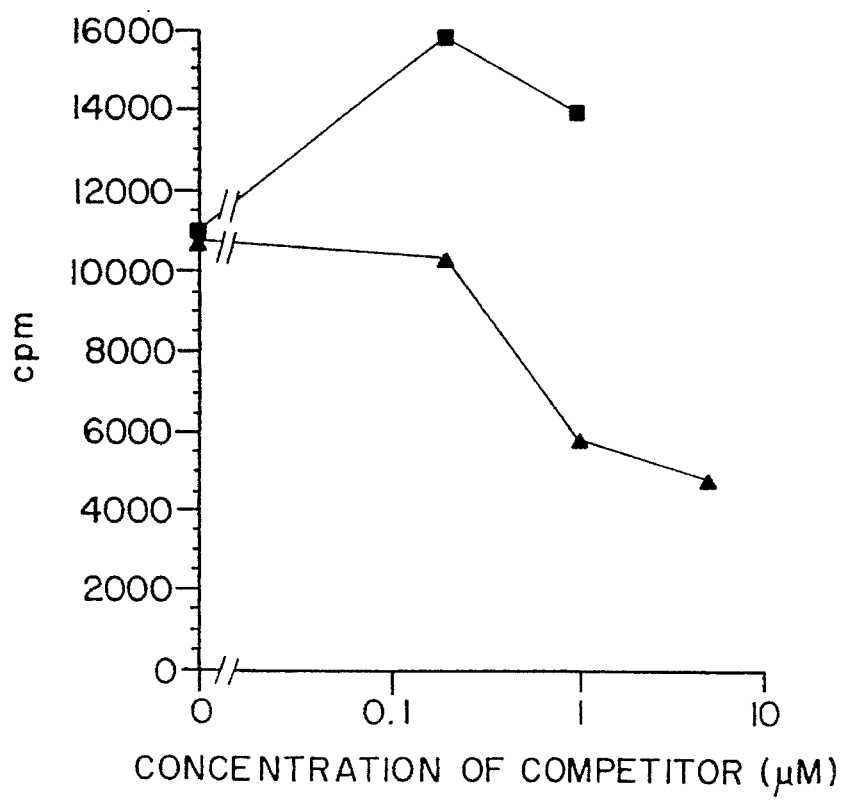

Besides competing for 14 kDa-fibronectin binding, the excess unlabeled 14 kDa fragment also competed for fibronectin-fibronectin binding (FIG. 6B). At the highest concentration tested (5 μM), the 14 kDa fragment inhibited the binding of fibronectin to fibronectin by more than 50%. As with 14 kDa-fibronectin binding, unlabeled fibronectin did not compete for the fibronectin-fibronectin binding, probably for the reasons mentioned above. Thus, the 14 kDa fragment of fibronectin that inhibited matrix assembly, also binds to fibronectin directly, and inhibits fibronectin-fibronectin association.

Example VI

Synthetic subfragments of the 14 kDa polypeptide

Four polypeptides (of 30–34 amino acids each) were synthesized, representing the region of fibronectin encompassed by the 14 kDa fragment (polypeptides P1, P2, P3, and P4). These polypeptides were tested for inhibition of the 14 kDa-fibronectin association as follows. Plastic wells were coated with 5 μg/ml fibronectin, blocked with BSA, then probed with $^{125}$I-labeled 14 kDa fragment (FIG. 7A), or $^{125}$I-labeled fibronectin (FIG. 7B), in the presence of various concentrations of unlabeled heparin-binding fragments (■), polypeptide P1 (◆), polypeptide P2 (▲), polypeptide P3 (□) or an α$_5$ cytoplasmic domain polypeptide as a negative control (○). The solutions were incubated for 2 hours at 37° C., followed by extensive washing with 0.2% BSA in PBS, and measurement of the radioactivity bound to the wells. The concentration values shown in FIGS. 7A and B for heparin-binding fragments refer to the final concentrations of the 14 kDa fragment in the solutions.

Figure 7A:
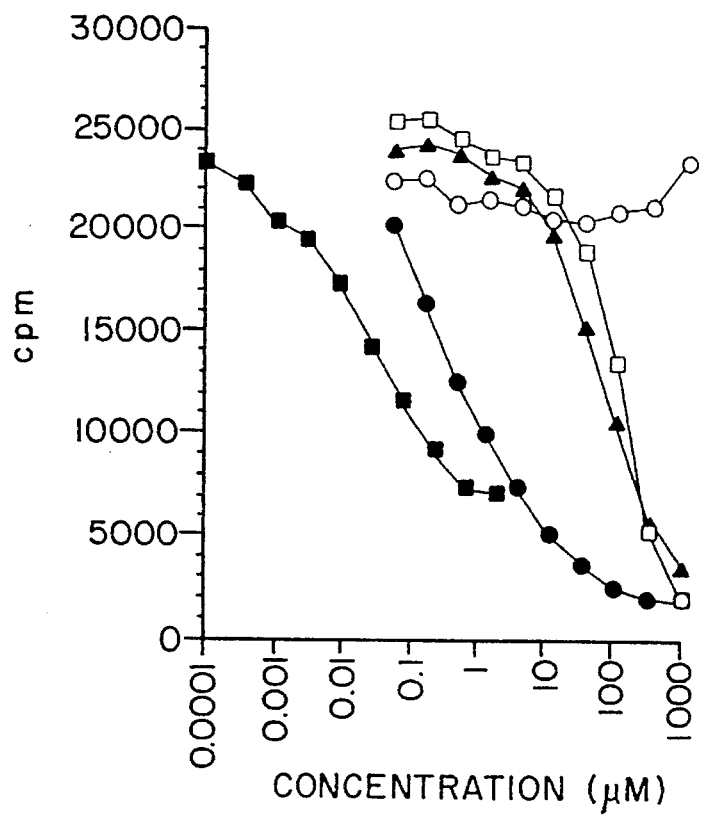

Polypeptide P1 was the most efficient at inhibiting the binding of the 14 kDa fragment to fibronectin, with an IC$_{50}$ of 1 μM; polypeptides P2 and P3 were approximately 100-fold less potent (FIG. 7A). Polypeptide P4 did not significantly inhibit the 14 kDa-fibronectin association, rather, at concentrations above 100 μM, it stimulated this association. The reason for the enhancement of binding by polypeptide P4 is not clear; it is possible that polypeptide P4 represents part of a fibronectin binding domain. However, since polypeptide P4 did not inhibit the binding of 14 kDa to fibronectin it is not likely to be as important in fibronectin self-association as the polypeptide P1 region. As shown in FIG. 7, a non-related polypeptide (a polypeptide representing the cytoplasmic domain of the integrin α$_5$ subunit) had no effect on 14 kDa-fibronectin association.

Figure 7B:
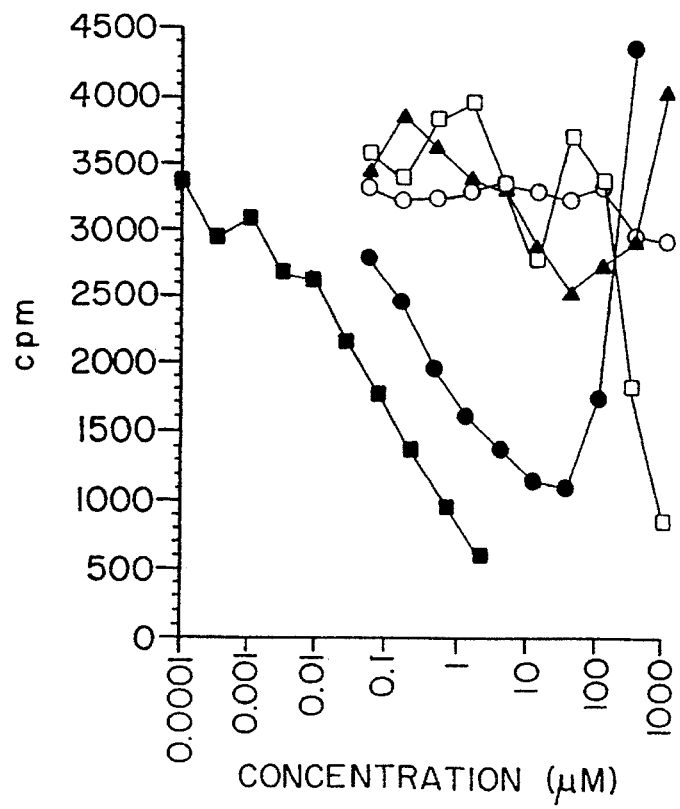
FIG. 7B illustrates the inhibition of fibronectin-fibronectin binding by polypeptides P1, P2, P3 and P4 from the 14 kDa region.

Since the 14 kDa fragment was found to inhibit fibronectin-fibronectin association, it was next tested whether any of the polypeptides representing the 14 kDa region could also inhibit the binding of fibronectin to itself. Once again polypeptide P1 proved to be the most potent, inhibiting fibronectin self-association with an IC$_{50}$ of approximately 1 μM (FIG. 7B). The only other polypeptide that significantly inhibited fibronectin-fibronectin binding was polypeptide P3 with an IC$_{50}$ of 200–300 μM (FIG. 7B).

One unexpected result was found. While polypeptide P1 inhibited fibronectin-fibronectin association at low concentrations (0.1 to 50 μM), at high concentrations it actually enhanced the binding of fibronectin to the wells (FIG. 7B). At high concentrations, it has been found that polypeptide P1 aggregates and can be pelleted by high speed centrifugation. This phenomenon does not occur with polypeptide P2. It is possible that at high concentrations polypeptide P1 aggregates into multimers and binds to the coated fibronectin and that the $^{125}$I-fibronectin probe becomes incorporated into these polypeptide P1/fibronectin complexes. This could lead to the observed increase in signal seen with P1 concentrations above 100 μM, because as shown below, fibronectin binds directly to polypeptide P1. Moreover, this explanation was supported by the demonstration that polypeptide P1 could be pelleted by centrifugation from solutions containing more than 100 μM of polypeptide. Thus, the ability of the 14 kDa fragment to inhibit fibronectin-fibronectin binding was also shared by polypeptide P1, which was modeled after the amino terminal 31 residues of the 14 kDa fragment.

The inhibition of fibronectin-fibronectin association by polypeptide P1 implies that P1 binds to fibronectin. To study the binding of fibronectin to P1 or the other polypeptides, the polypeptides were covalently linked to Sepharose beads, and the resins were tested in affinity chromatography assays by using human plasma as a source of fibronectin.

Figure 8:
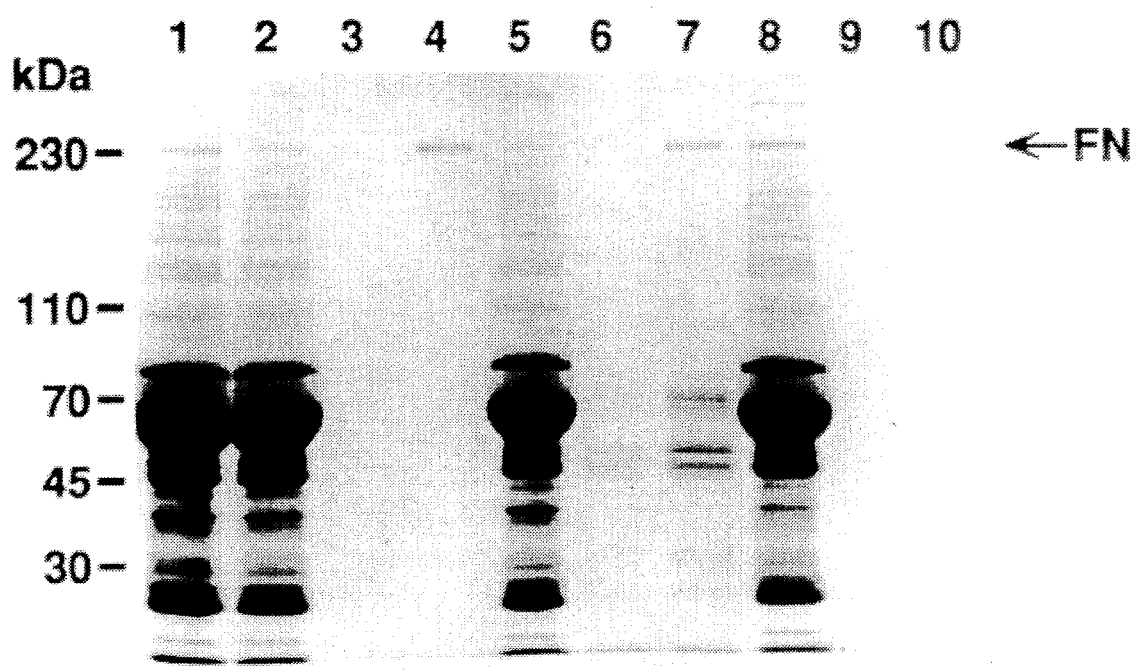
FIG. 8 illustrates the binding of plasma fibronectin to polypeptide P1 and polypeptide P2 in affinity chromatography.

With respect to FIG. 8, human plasma was applied to either gelatin-Sepharose (lanes 2–4) or columns made of polypeptide P1 (lanes 5–7) or P2 (lanes 8–10) coupled to Sepharose. The unbound fraction of proteins was collected, the columns were washed with PBS+5 mM EDTA (PBS/EDTA), followed by 0.2M NaCl in PBS/EDTA. Proteins remaining bound to the columns were eluted with 8M urea in PBS/EDTA. Lane 1 contains starting material. Lanes 2, 5 and 8 are the flow-through fractions from the gelatin, P1, and P2, columns, respectively. Lanes 3–4, 6–7, and 9–10 are the first and second urea eluates from the gelatin, P1, and P2, columns, respectively. The positions of molecular mass standards are indicated to the left of the figure. The position of fibronectin is indicated to the right of the figure.

Upon inspection of FIG. 8, it is seen that most of the fibronectin was removed from plasma by passage over either a gelatin or a P1 column (FIG. 8, lanes 2 and 5). The capacity of the P1 column for fibronectin was comparable to that of gelatin-Sepharose, which is known to be 0.5 mg fibronectin/mg gelatin [Engvall and Ruoslahti, supra]. The bound fibronectin was not eluted by 0.3M NaCl, but it was completely removed from both the gelatin and P1 columns by 8M urea (FIG. 8, lanes 3, 4, 6 and 7). A solution of P1 will also elute fibronectin from the P1 column. The preparation eluted from the P1 column with 8M urea (FIG. 8) contained some other plasma proteins, but was greatly enriched in fibronectin. No fibronectin bound to a P2 column (FIG. 8, lanes 8–10) or to a plain Sepharose control column. This indicates that fibronectin binds efficiently to polypeptide P1, but not to polypeptide P2. Thus, polypeptide P1 shares two of the characteristics of the 14 kDa fragment, the ability to bind fibronectin, and the ability to inhibit fibronectin self-association.

Figure 9A:
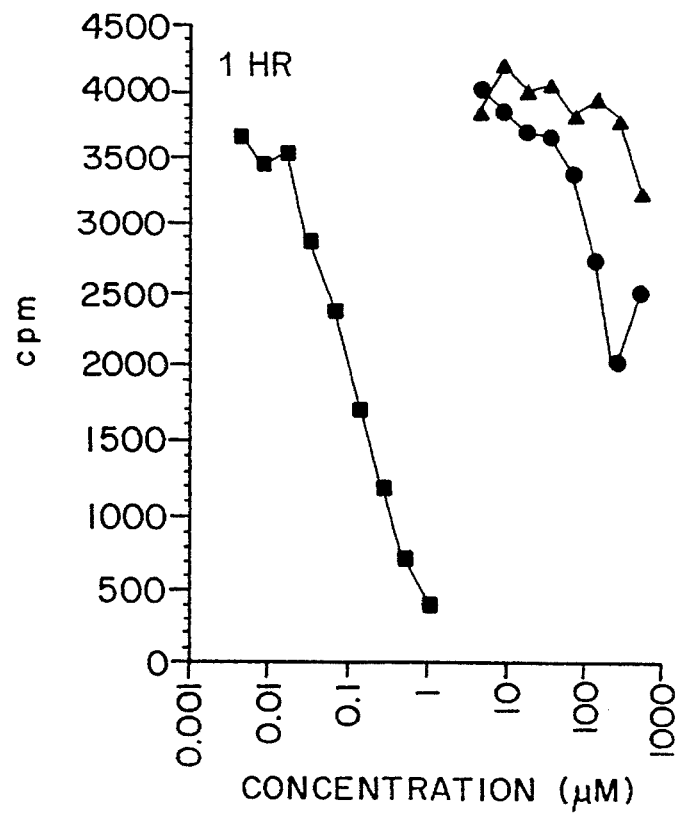
FIG. 9 illustrates the inhibition of fibronectin matrix assembly by polypeptide P1 and P2 after one hour (FIG. 9A) and after 24 hours (FIG. 9B).
Figure 9B:
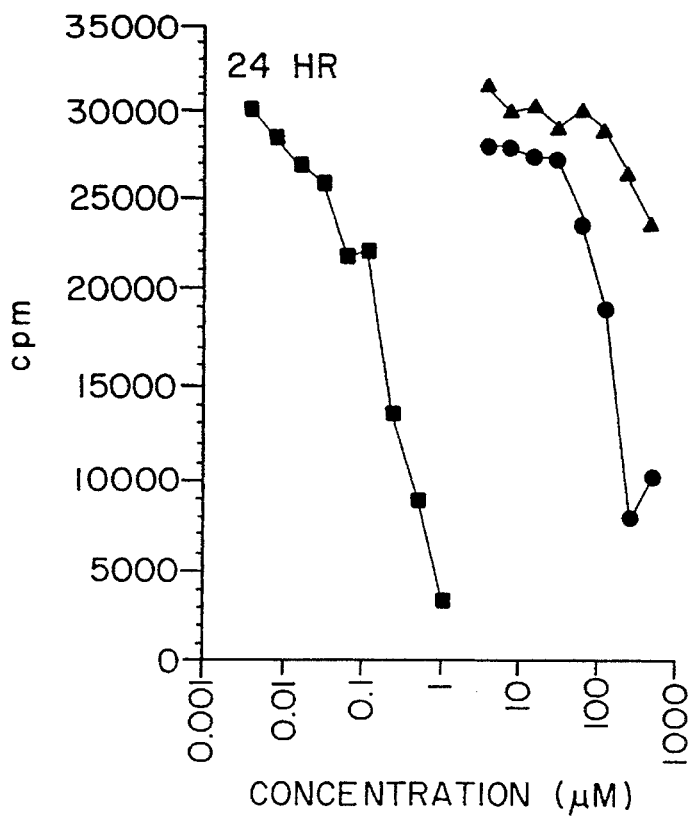

There is yet a third similarity between polypeptide P1 and the 14 kDa fragment. Confluent monolayers of IMR-90 cells were incubated with $^{125}$I-fibronectin in the presence of various concentrations of unlabeled fibronectin (■), polypeptide P1 (●) or polypeptide P2 (▲). In FIG. 9A, cells were incubated for one hour, washed, and the total bound radioactivity was measured. In FIG. 9B, cells were incubated for 24 hours, washed, and the total amount of $^{125}$I-fibronectin was measured. Each data point is the average of duplicate determinations.

Testing of polypeptides P1–P4 in the 1 hour matrix assembly assay showed that, among the four polypeptides, polypeptide P1 inhibited the binding of $^{125}$I-fibronectin to cells most efficiently, by approximately 40–50% (FIG. 9A). The other polypeptides were less effective than P1 in the 1 hour assay, typically inhibiting by no more than 25% (the result for P2 is shown in FIG. 9A).

As with the 14 kDa fragment, polypeptide P1 dramatically reduced the incorporation of fibronectin into the matrix in a 24 hour assay (FIG. 9B). The other polypeptides had only marginal effects (FIG. 9B shows results obtained with P2). The effect with polypeptide P2 seems to be non-specific since a polypeptide modeled after the cytoplasmic domain of the integrin $\alpha_5$ subunit had an equivalent effect. Maximal inhibition of the incorporation of fibronectin into the matrix by approximately 80% was obtained at a polypeptide P1 concentration of 250–500 μM.

Cells that were treated with polypeptide P1 at concentrations above 500 μM exhibited an unusually high level of $^{125}$I-fibronectin signal in the matrix assembly assay. As mentioned above, polypeptide P1 tended to aggregate at high concentrations. It is possible that at concentrations above 500 μM polypeptide P1 aggregated on cell surfaces, or onto the plastic surface, and thereby caused adsorption of $^{125}$I-fibronectin.

To determine whether polypeptide P1 and the 70 kDa fragment could cooperate in the inhibition of matrix assembly, mixing experiments were done by treating cells with a constant amount of unlabeled 70 kDa (0.03 μM), and adding various amounts of polypeptide P1 (from 0–500 μM). In the presence of the 70 kDa fragment, the maximal inhibition by polypeptide P1 was obtained at a concentration of 250–500 μM. Thus, there was no increase in the effective concentration for inhibition by polypeptide P1 in the presence of the 70 kDa fragment and the combined effect was additive, not synergistic.

The data presented above demonstrates that polypeptide P1 inhibits matrix assembly in a manner similar to that of the 14 kDa fragment. Both the 14 kDa fragment and polypeptide P1 have a small effect on the binding of fibronectin to cell surfaces, but both significantly inhibit the incorporation of fibronectin into the extracellular matrix.

Example VII

Effect of 14 kDa polypeptide on endogenous fibronectin matrix assembly

Figure 10:
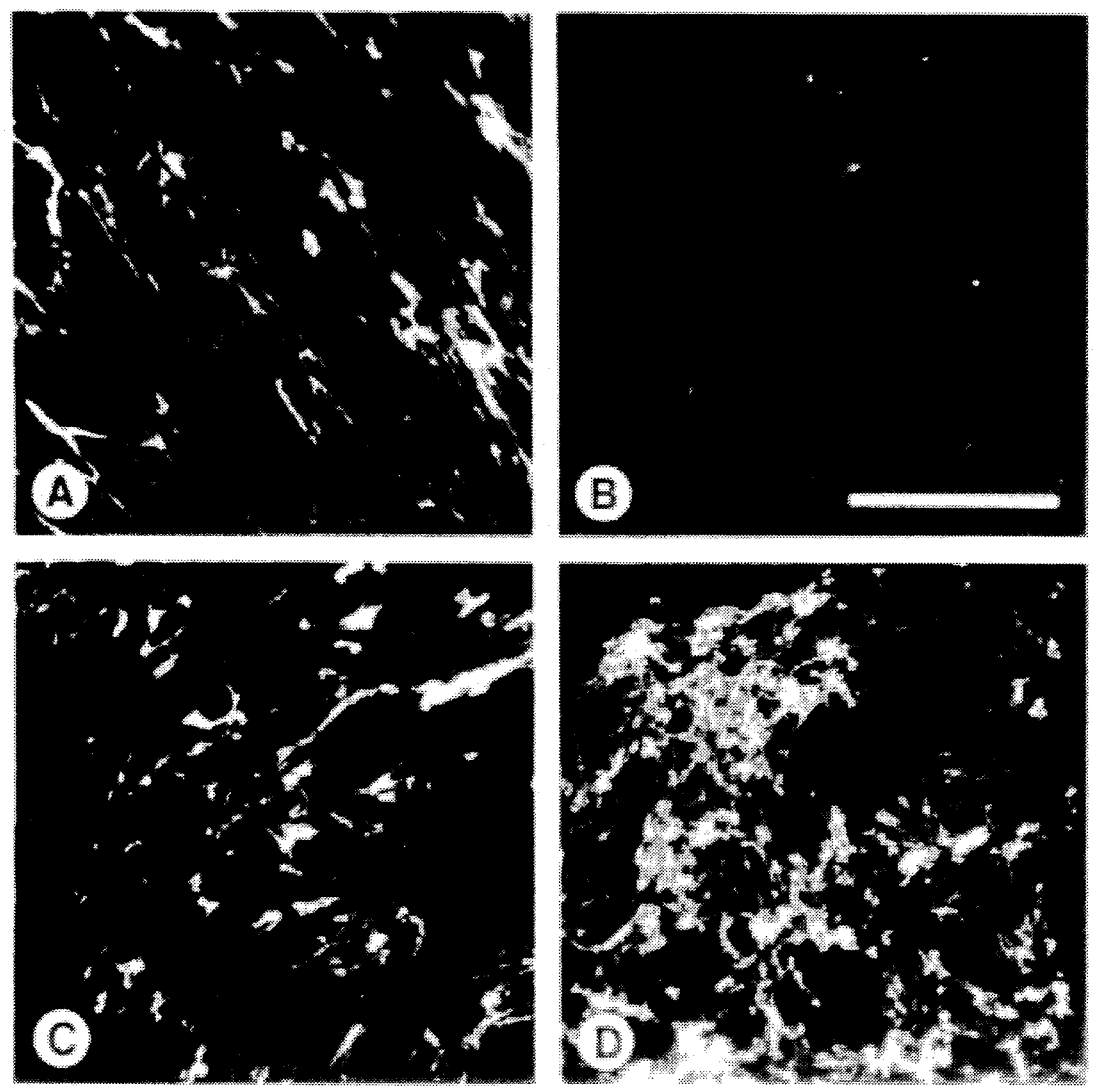

All of the experiments presented thus far have focussed on the assembly of exogenous fibronectin into the matrix. The effect of the 14 kDa polypeptides on endogenous fibronectin matrix assembly has also been studied. IMR-90 cells were seeded onto slides that had been precoated with collagen type I. After attaching for 1 hour at 37° C., cells were cultured for 48 hours in 10% fibronectin-deficient medium plus either no additions (FIG. 10A), or 1 mg/ml 70 kDa fragment (FIG. 10B), or 500 μM polypeptide P1 (FIG. 10C), or 500 μM polypeptide P2 (FIG. 10D). Cells were then fixed with paraformaldehyde and the fibronectin in the matrix was visualized with rhodamine labeled antifibronectin antibodies as described above. The panels in FIG. 10 show representative fields from each culture. Bar equals 25 μm.

Shortly after seeding, cells were grown in the presence of various concentrations of the 70 kDa fragment, or polypeptides P1 or P2 for 48 hours. As shown previously [McDonald et al., supra], high concentrations of the 70 kDa fragment inhibited endogenous matrix assembly (FIG. 10B). Subconfluent cultures were studied because it has been found that the effect of the polypeptides on matrix assembly was more pronounced in subconfluent cultures than in confluent cultures. Polypeptide P1 was the most effective at disrupting endogenous fibronectin matrix assembly. As seen in FIG. 10C, in the presence of polypeptide P1 only short stitches of matrix were seen on the cells, and those stitches were usually located at the edges of cells, with little or no fibrils located above or beneath the cell bodies. However, in the presence of polypeptide P2 an extensive matrix surrounded the cells (FIG. 10D). Thus polypeptide P1 disrupted endogenous fibronectin matrix assembly, while polypeptide P2 did not.

Example VIII

Promotion of cell attachment

To determine whether fibronectin which is bound to polypeptide P1 is capable of supporting cell adhesion, plastic wells were coated with polypeptide P1, then fibronectin in solution was bound to the coated polypeptide, and cells were seeded onto this substrate to assay the extent of cell adhesion. Two experiments were then performed.

In the first experiment, polypeptide P1 and a control polypeptide (representing the cytoplasmic domain of the integrin $\alpha_4$ subunit) were coated onto plastic wells at various concentrations in the presence of 0.1M $Na_2CO_3$, pH 9.5, and 0.25% glutaraldehyde. The wells were then blocked with 1% BSA in PBS, followed by the addition of 250 µg/ml of fibronectin, 1% BSA, in PBS. After incubation with this solution of fibronectin and BSA for 3 hours, the wells were washed, and IMR-90 cells were seeded onto the dishes for one hour at 37° C. in media lacking calf serum.

Figure 11A:
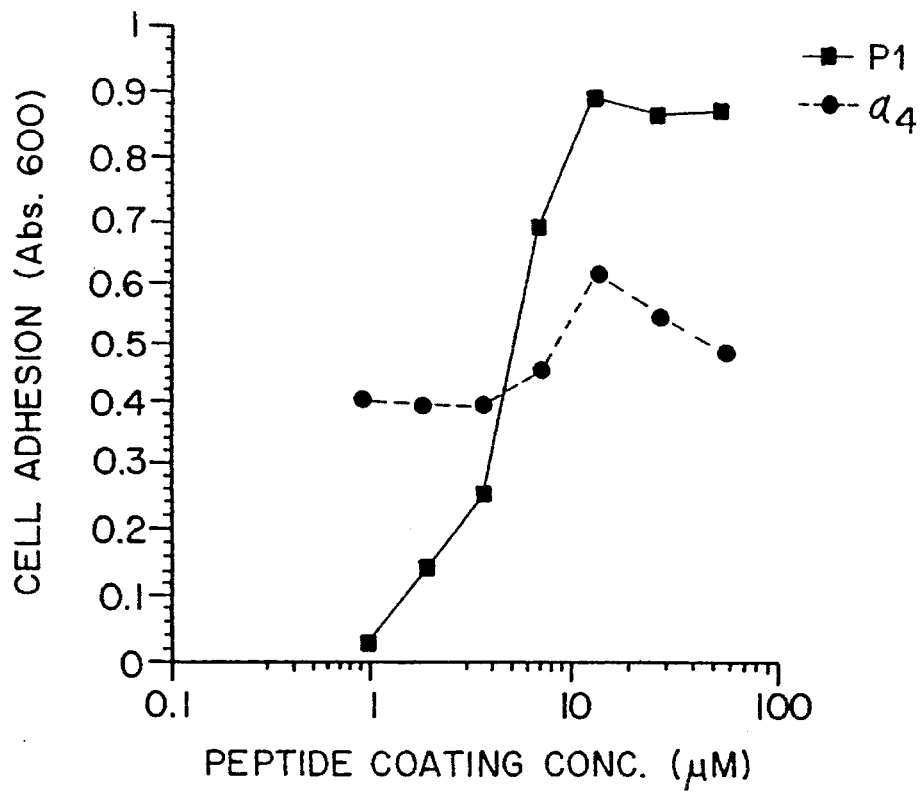
FIG. 11 illustrates the variation cell attachment to fibronectin which is bound to a polypeptide P1-coated substrate or $\alpha_4$-coated substrate as the concentration of P1 is increased (FIG. 11A) or as the concentration of fibronectin is increased (FIG. 11B).
Figure 11B:
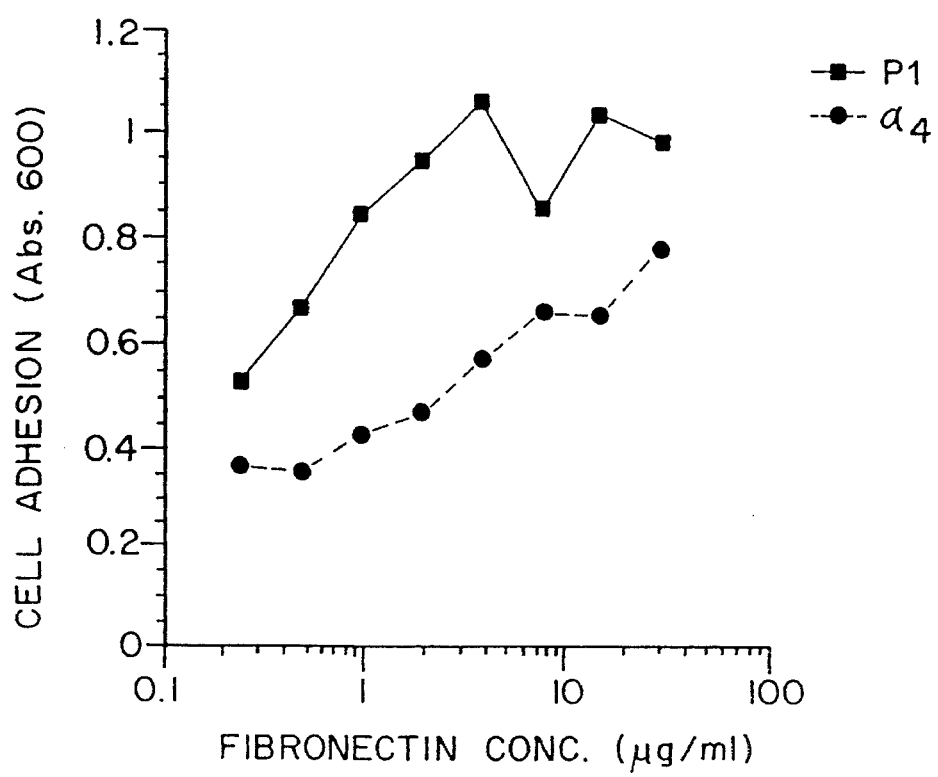

The degree of cell attachment was quantitated by staining cells with 0.5% Crystal Violet, 50% ethanol, and measuring the amount of dye bound to the cells in the wells. As shown in FIG. 11, panel A, polypeptide P1 supported cell adhesion in a dose dependent manner after binding fibronectin. When no polypeptide was coated onto the dish, no cell adhesion was detected, indicating that polypeptide P1 was required for cell adhesion. The control polypeptide gave a relatively high background (as can be seen by the amount of cell adhesion even at low levels of polypeptide $\alpha_4$ coating), and did not support significantly greater cell adhesion at higher levels of polypeptide coating, indicating a non-specific adhesion of cells to the wells coated with the $\alpha_4$ polypeptide.

In the second experiment, a constant concentration (1 mM) of polypeptide P1 (or $\alpha_4$) was coated onto the plastic wells, the wells were blocked with 1% BSA, and then various concentrations of fibronectin in 1% BSA were incubated for 3 hours with the polypeptide-coated wells. After washing the wells, IMR-90 cells were seeded onto the wells and the degree of cell adhesion was determined as described above. As shown in FIG. 11, panel B, polypeptide P1 supported a higher degree of cell adhesion than did polypeptide $\alpha_4$. This cell adhesion required incubation with fibronectin, since the degree of cell adhesion was directly related to the concentration of fibronectin in solution.

The above data indicate that fibronectin binds to polypeptide P1 which is coated onto a substrate, and that the bound fibronectin is capable of supporting cell adhesion, thereby demonstrating that polypeptide P1 is useful for promoting cell attachment.

While the invention has been described in detail with reference to certain preferred embodiments thereof, it will be understood that modifications and variations are within the spirit and scope of that which is described and claimed.

SUMMARY OF SEQUENCES

Sequence ID No. 1 is the amino acid sequence of the novel polypeptide fragment of fibronectin, according to the present invention (i.e., the 14 kDa fragment).

Sequence ID No. 2 is the amino acid sequences of a synthetic polypeptide (i.e., P1) which mimics the fibronectin binding properties of the polypeptide of Sequence ID No. 1.

Sequence ID Nos. 3–5 present the amino acid sequences of synthetic polypeptides derived from the 14 kDa sequence of the invention.

---

That which is claimed is:

1. A substantially purified polypeptide related to the III$_I$ repeat of fibronectin comprising the amino acid sequence set forth in SEQ ID NO: 1 and having a molecular weight of about 14 kDa, wherein said polypeptide has the ability to bind to fibronectin directly and to substantially reduce fibronectin matrix assembly, while not reducing substantially the ability of fibronectin to bind to cells.

2. A polypeptide according to claim 1, wherein said polypeptide is further characterized by:

being capable of inhibiting fibronectin-fibronectin association.

3. A polypeptide according to claim 1, wherein said polypeptide is further characterized by:

binding specifically to IMR-90 cells, but not to HT-1080 cells.

4. A substantially purified polypeptide related to the III$_I$ repeat of fibronectin having a molecular weight of about 14 kDa and having the amino acid sequence set forth in SEQ ID NO: 1, wherein said polypeptide has the ability to bind to fibronectin directly and to substantially reduce fibronectin matrix assembly, while not reducing substantially the ability of fibronectin to bind to cells.

5. A polypeptide fragment of a 14 kDa polypeptide related to the II$_I$ repeat of fibronectin, wherein said fragment is selected from the group consisting of P1, P2, P3, and P4, wherein P1 has the amino acid sequence shown in SEQ ID NO: 2; P2 has the amino acid sequence shown in SEQ ID NO: 3; P3 has the amino acid sequence shown in SEQ ID NO: 4; and P4 has the amino acid sequence shown in SEQ ID NO: 5.

6. A composition comprising at least two of the peptides of claim 5.

* * * * *

UNITED STATES PATENT AND TRADEMARK OFFICE
CERTIFICATE OF CORRECTION

PATENT NO. : 5,453,489
DATED : September 26, 1995
INVENTOR(S) : Ruoslahti et al.

It is certified that error appears in the above-indentified patent and that said Letters Patent is hereby corrected as shown below:

In column 2, line 57, please insert --70-- between "the" and "kDa"

In column 2, line 64, please delete "binding" after "kDa-fibronectin" and "binding"

In column 4, line 66, please delete the space between "(" and "for"

In column 8, line 8, please superscript the "125" in "125I-fibronectin"

In column 11, line 60, please insert --I-- between "$^{125}$" and "-14 kDa"

In claim 5, column 20, line 15, please delete "$II_I$" and replace therefor with --$III_I$--

Signed and Sealed this

Fourteenth Day of July, 1998

Attest:

BRUCE LEHMAN

*Attesting Officer*     *Commissioner of Patents and Trademarks*